United States Patent [19]

Auer et al.

[11] 4,156,691

[45] May 29, 1979

[54] PRODUCTION OF METHYL-[2-(2,4,6-TRIBROMOPHENYLCAR-BAMOYL-)ETHYL-]PHOSPHINIC ACID

[75] Inventors: Eberhard Auer; Alexander Ohorodnik, both of Erftstadt; Paul Stutzke, Bornheim-Walberberg, all of Fed. Rep. of Germany

[73] Assignee: Hoechst Aktiengesellschaft, Frankfurt am Main, Fed. Rep. of Germany

[21] Appl. No.: 907,026

[22] Filed: May 17, 1978

[30] Foreign Application Priority Data

May 23, 1977 [DE] Fed. Rep. of Germany ....... 2723137

[51] Int. Cl.$^2$ .............................................. C07F 9/30

[52] U.S. Cl. ................................................. 260/502.5

[58] Field of Search ..................................... 260/502.5

[56] References Cited

U.S. PATENT DOCUMENTS 3,980,614  9/1976  Noetzel et al. ..................... 260/502.5

Primary Examiner—Joseph E. Evans
Attorney, Agent, or Firm—Connolly and Hutz

[57] ABSTRACT

Methyl-[2-(2,4,6-tribromophenylcarbamoyl-)ethyl-]phosphinic acid is made continuously. To this end, molten 2-methyl-2,5-dioxo-1-oxa-2-phospholane is reacted with molten 2,4,6-tribromoaniline at 210° to 250° C. in the absence of a solvent.

2 Claims, 1 Drawing Figure

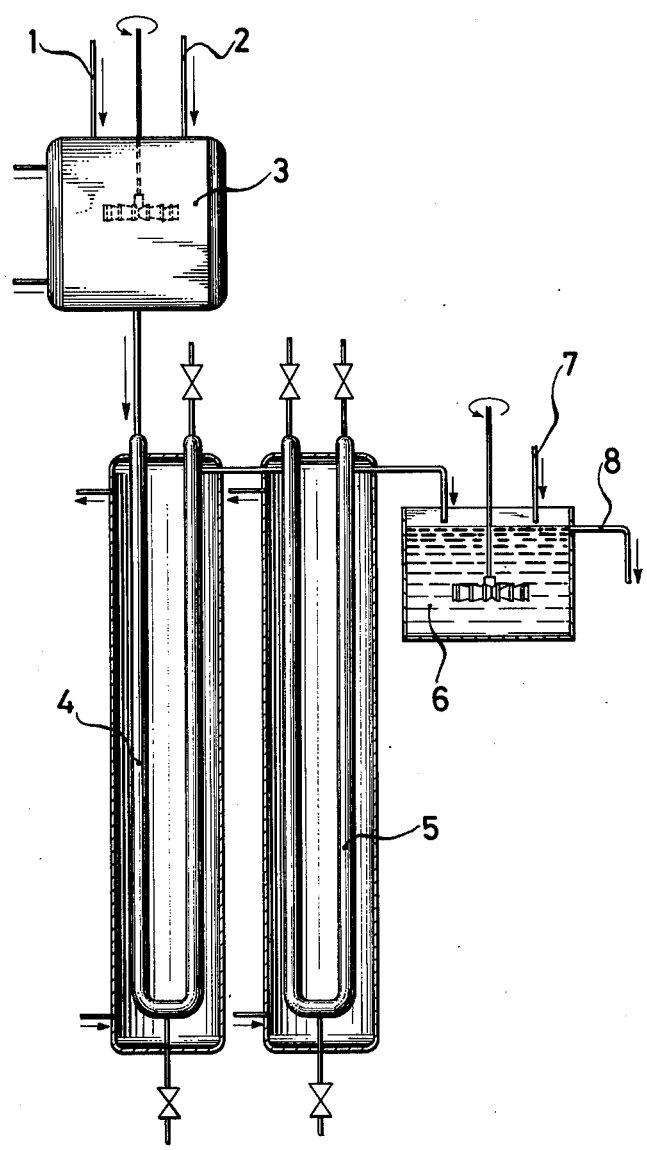

PRODUCTION OF METHYL-[2-(2,4,6-TRIBROMOPHENYLCARBAMOYL-)ETHYL-]PHOSPHINIC ACID

It is known that methyl-[2-(2,4,6-tribromophenylcarbamoyl-)ethyl-]phosphinic acid can be made by reacting 2-methyl-2,5-dioxo-1-oxa-2-phospholane with 2,4,6-tribromoaniline (cf. German Patent Specification "Offenlegungsschrift" No. 2 511 185).

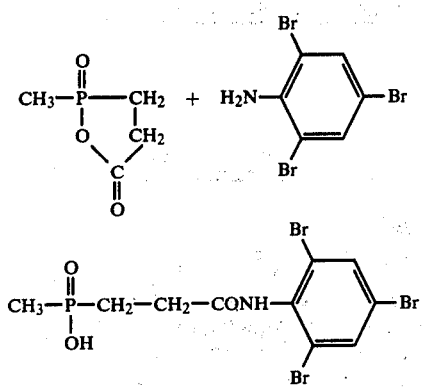

In this process, the two starting reactants are dissolved in o-dichlorobenzene and reacted at 180° to 200° C. The reaction product, which is insoluble in o-dichlorobenzene, can be recovered therefrom in pure form by filtration and removal of solvent residues.

The process just described is not, however, fully satisfactory inasmuch as it is not very suitable for use on an industrial scale for the following reasons: At 180° to 200° C., the reaction proceeds at low speed over the long period of 4 hours. In addition to this, rather large quantities of organic solvent (2 to 3 liter per kg of final product) which in the end have to be separated are used.

The present invention, which unexpectedly enables the above disadvantageous phenomena to be obviated, relates more specifically to a process for the continuous manufacture of methyl-[2-(2,4,6-tribromophenylcarbamoyl-)ethyl-]phosphinic acid by reacting 2-methyl-2,5-dioxo-1-oxa-2-phospholane with 2,4,6-tribromoaniline, which comprises: melting the starting reactants and reacting the melt at 210° to 250° C. in the absence of a solvent.

A preferred feature of the present process provides for the molten starting reactants to be continually mixed in a mixing zone at 122° to 140° C. over a period of 1 to 30 minutes; for the resulting mixture to be passed initially within 2 to 30 minutes through a first tubular reaction zone heated to 210° to 233° C. and then within 2 to 30 minutes through a second tubular reaction zone heated to 227° to 250° C., the second reaction zone being maintained at a temperature which is at least 5° C. higher than the temperature prevailing in the first reaction zone; for the resulting molten reaction product to be quenched with water, to be disintegrated, to be separated from the water, and to be dried at 30° to 100° C.

A further preferred feature of the present process provides for a stoichiometric excess of 2-methyl-2,5-dioxo-1-oxa-2-phospholane to be used in order to reduce the melting point.

The reactants are substantially not liable to undergo reaction inside the mixing zone if mixed together at a temperature slightly above the melting point of 2,4,6-tribromoaniline (122° C.) in a mixing zone whose dimensions permit the residence time of the melt in said zone to be limited to at most 30 minutes.

Needless to say the reaction inside the tubular reactor is terminated the sooner the higher the reaction temperature selected. In view of the fact that the final product in pure form has a melting point of 250° C. and that it is preferable for the reaction to be carried out in liquid phase, it is good practice to maintain at least the final temperature of the reaction melt at that level.

The reaction at 250° C. has more particularly been found to produce a 90% conversion rate within 3 minutes. At that temperature, the final product is however liable to undergo gradual decomposition and undesirable coloration. To avoid this, the present process provides for the reaction to be effected at a lower temperature over a prolonged period in the reactor, so that it is possible for unreacted proportions of starting reactants to reduce the melting point, and for the reaction mixture to be heated to higher temperature just upstream of the reactor outlet so as to increase to conversion rate. As results therefrom, the reaction is effected in a plurality of stages at different temperatures.

In order to reduce the reaction temperature and maintain the liquid phase, it is also possible to use one of the two reactants, preferably 2-methyl-2,5-dioxo-1-oxa-2-phospholane, in excess.

It is more particularly possible to reduce the melting point as shown in the following Table 1:

| Content of phospholane in final product | Melting point of mixture |
|---|---|
| 3 weight % | 243° C. |
| 5 weight % | 238° C. |
| 10 weight % | 228° C. |
| 15 weight % | 222° C. |

If the melt were allowed to remain over a prolonged period of time at high temperature, it would be liable to undergo decomposition. To avoid this, the reaction melt is quenched just downstream of the outlet of the tubular reactor. To this end, it is preferably introduced into cold water in which the reaction product can be disintegrated, e.g. by means of a suitable mixer, and purified simultaneously. The dark colored decomposition products and the excess proportion, if any, of 2-methyl-2,5-dioxo-1-oxa-2-phospholane are found to dissolve in the water, in which methyl-[2-(2,4,6-tribromophenylcarbamoyl-)ethyl-]phosphinic acid is insoluble. The "phosphinic acid" suspension can be separated from the water by filtration, centrifugation or the like. After the filter cake has been dried, preferably in a fluidized bed drier, it is possible to obtain the "phosphinic acid" in the form of a white powder. The fluidized bed drier also enables residual unreacted 2,4,6-tribromoaniline to be exhausted so that inodorless final product will be obtained.

Methyl-[2-(2,4,6-tribromophenylcarbamoyl-)ethyl-]phosphinic acid is known to be suitable for use as a flame retardant agent in polymeric moulding compositions.

EXAMPLE 1 (With reference to accompanying drawing)

A mixing vessel 3 (volume=370 ml) was maintained at 130° C. by means of a thermostat and fed with 600 ml/h (=1410 g/h=4.273 mol/h) of molten 2,4,6-tribromoaniline (coming from a conduit 1) and with 450 ml/h (=590 g/h=4.403 mol/h) of molten 2-methyl-2,5-dioxo-1-oxa-2-phospholane (coming from a conduit 2). The residence time in the mixing vessel 3 was 21 minutes.

The homogeneous mixture was continuously introduced into a first reactor 4 which was a jacketed U-tube 8 mm wide and 150 mm long (volume=75 ml), heated to 230° C.

Next, the reaction mixture was delivered to a second reactor 5 which had the same dimensions as the reactor 4 but was heated to 245° C. In each of the reactors 4 and 5, the residence time was 4.3 minutes. The liquid reaction mixture was continuously run into a water container 6, in which it was disintegrated by means of a suitable mixer and suspended. 20 l/h of water was admitted through a a conduit 7 and the suspension was taken from a conduit 8. The final product, which was methyl-[2-(2,4,6-tribromophenylcarbamoyl-)ethyl-]phosphinic acid was delivered to a continuous bulk centrifuge, separated from water therein and dried in a fluidized bed drier at 80° C.

The yield was 1760 g/h, corresponding to 88.7% of the theoretical, based on the 2,4,6-tribromoaniline used.

The product which was almost white had a slight greyisch tinge and a melting point of 243° to 245° C.

EXAMPLES 2 to 4

The reactions were effected as in Example 1. The reactors were U-tubes 12 mm wide and 160 mm long (volume of each reactor=180 ml). 2,4,6-tribromoaniline was used at a rate of 600 ml/h. The other conditions are indicated in the following Table 2.

TABLE 2

| Ex. | Phospholane ml/h | Temperature °C. 1st reactor | Temperature °C. 2nd Reactor | Residence time in each reactor min | Yield (g/h) | Yield (% of theoretical) | Melting point (°C.) |
|---|---|---|---|---|---|---|---|
| 2 | 480 | 220 | 240 | 10 | 1830 | 92.3 | 244 to 246 |
| 3 | 520 | 220 | 230 | 9.6 | 1710 | 86.2 | 248 to 250 |
| 4 | 570 | 220 | 230 | 9.2 | 1800 | 90.8 | 249 |

We claim:

1. A process for the continuous manufacture of methyl-[2-(2,4,6-tribromophenylcarbamoyl-)ethyl-]phosphinic acid by reacting 2-methyl-2,5-dioxo-1-oxa-2-phospholane with 2,4,6-tribromoaniline, which comprises melting the starting reactants and continually mixing them in a mixing zone at 122° to 140° C. over a period of 1 to 30 minutes, passing the resulting mixture initially within 2 to 30 minutes through a first tubular reaction zone heated to 210° to 233° C. and then within 2 to 30 minutes through a second tubular reaction zone heated to 227° to 250° C., the second reaction zone being maintained at a temperature which is at least 5° C. higher than the temperature prevailing in the first reaction zone, quenching the resulting molten reaction product with water, disintegrating it, separating it from the water, and drying it at 30° to 100° C.

2. A process as claimed in claim 1, wherein a stoichiometric excess of 2-methyl-2,5-dioxo-1-oxa-2-phospholane is used.

* * * * *